(12) United States Patent
McKiernan et al.

(10) Patent No.: US 8,502,010 B2
(45) Date of Patent: Aug. 6, 2013

(54) ABSORBENT ARTICLE HAVING A POTTY TRAINING READINESS INDICATOR

(75) Inventors: Robin Lynn McKiernan, Mason, OH (US); Thomas James Klofta, Cincinnati, OH (US); Donald Carroll Roe, West Chester, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 1014 days.

(21) Appl. No.: 12/043,980

(22) Filed: Mar. 7, 2008

(65) Prior Publication Data

US 2008/0228157 A1 Sep. 18, 2008

Related U.S. Application Data

(60) Provisional application No. 60/906,044, filed on Mar. 9, 2007.

(51) Int. Cl.
*A61F 13/15* (2006.01)

(52) U.S. Cl.
USPC .......................................................... 604/361

(58) Field of Classification Search
USPC .......................................................... 604/361
See application file for complete search history.

(56) References Cited

U.S. PATENT DOCUMENTS

| | | | |
|---|---|---|---|
| 3,848,594 A | 11/1974 | Buell | |
| 3,860,003 A | 1/1975 | Buell | |
| 4,022,211 A | 5/1977 | Timmons et al. | |
| 4,231,370 A | 11/1980 | Mroz et al. | |
| 4,381,781 A | 5/1983 | Sciaraffa et al. | |
| 4,610,678 A | 9/1986 | Weisman et al. | |
| 4,662,875 A | 5/1987 | Hirotsu et al. | |
| 4,673,402 A | 6/1987 | Weisman et al. | |
| 4,681,576 A | 7/1987 | Colon et al. | |
| 4,699,622 A | 10/1987 | Toussant et al. | |
| 4,743,238 A | 5/1988 | Colon et al. | |
| 4,834,735 A | 5/1989 | Alemany et al. | |
| 4,846,815 A | 7/1989 | Scripps | |
| 4,857,067 A | 8/1989 | Wood et al. | |
| 4,888,231 A | 12/1989 | Angstadt | |
| 4,894,060 A | 1/1990 | Mestegard | |
| 4,895,567 A | 1/1990 | Colon et al. | |
| 4,938,753 A | 7/1990 | Van Gompel et al. | |
| 4,940,464 A | 7/1990 | Van Gompel et al. | |
| 4,946,527 A | 8/1990 | Battrell | |
| 4,963,140 A | 10/1990 | Robertson et al. | |
| 4,968,312 A | 11/1990 | Khan | |
| 4,990,147 A | 2/1991 | Freeland | |
| 5,035,691 A | 7/1991 | Zimmel et al. | |
| 5,062,840 A | 11/1991 | Holt et al. | |

(Continued)

FOREIGN PATENT DOCUMENTS

EP  0 847 738 A1  6/1998

OTHER PUBLICATIONS

International Search Report, PCT/IB2008/050822, mailed Sep. 30, 2008.

*Primary Examiner* — Lynne Anderson

(74) *Attorney, Agent, or Firm* — Andrew A Paul; Laura L. Whitmer

(57) ABSTRACT

A potty training readiness indicator, which can be utilized in a disposable absorbent article, having at least one indicating member. The potty training readiness indicator which indicates to the caregiver when the wearer is ready to be potty trained.

14 Claims, 11 Drawing Sheets

U.S. PATENT DOCUMENTS

| | | | |
|---|---|---|---|
| 5,066,711 A | 11/1991 | Colon et al. | |
| 5,092,861 A | 3/1992 | Nomura et al. | |
| 5,137,537 A | 8/1992 | Herron et al. | |
| 5,147,345 A | 9/1992 | Young et al. | |
| 5,151,092 A | 9/1992 | Buell et al. | |
| 5,171,236 A | 12/1992 | Dreier et al. | |
| 5,221,274 A | 6/1993 | Buell et al. | |
| 5,242,436 A | 9/1993 | Weil et al. | |
| 5,246,433 A | 9/1993 | Hasse et al. | |
| 5,260,345 A | 11/1993 | DesMarais et al. | |
| 5,269,755 A | 12/1993 | Bodicky | |
| 5,306,266 A | 4/1994 | Freeland | |
| 5,342,338 A | 8/1994 | Roe | |
| 5,342,861 A | 8/1994 | Raykovitz | |
| 5,387,207 A | 2/1995 | Dyer et al. | |
| 5,397,318 A | 3/1995 | Dreier | |
| 5,499,978 A | 3/1996 | Buell et al. | |
| 5,507,736 A | 4/1996 | Clear et al. | |
| 5,514,121 A | 5/1996 | Roe et al. | |
| 5,540,671 A | 7/1996 | Dreier | |
| 5,554,142 A | 9/1996 | Dreier et al. | |
| 5,554,145 A | 9/1996 | Roe et al. | |
| 5,569,234 A | 10/1996 | Buell et al. | |
| 5,571,096 A | 11/1996 | Dobrin et al. | |
| 5,580,411 A | 12/1996 | Nease et al. | |
| 5,591,152 A | 1/1997 | Buell et al. | |
| 5,625,222 A | 4/1997 | Yoneda et al. | |
| 5,653,703 A | 8/1997 | Roe et al. | |
| 5,669,897 A | 9/1997 | Lavon et al. | |
| 5,865,823 A | 2/1999 | Curro | |
| 5,897,545 A | 4/1999 | Kline et al. | |
| 5,938,648 A | 8/1999 | Lavon et al. | |
| 5,941,864 A | 8/1999 | Roe | |
| 5,957,908 A | 9/1999 | Kline et al. | |
| 5,977,430 A | 11/1999 | Roe et al. | |
| 5,997,520 A | 12/1999 | Ahr et al. | |
| 6,004,306 A | 12/1999 | Robles et al. | |
| 6,010,490 A | 1/2000 | Freeland et al. | |
| 6,013,063 A | 1/2000 | Roe et al. | |
| 6,013,589 A | 1/2000 | Desmarais et al. | |
| 6,075,178 A | 6/2000 | LaWilhelm et al. | |
| 6,083,211 A | 7/2000 | DesMarais et al. | |
| 6,120,487 A | 9/2000 | Ashton | |
| 6,120,489 A | 9/2000 | Johnson et al. | |
| 6,168,584 B1 | 1/2001 | Allen et al. | |
| 6,187,696 B1 | 2/2001 | Lim et al. | |
| 6,432,098 B1 | 8/2002 | Kline et al. | |
| 6,772,708 B2 | 8/2004 | Klofta et al. | |
| 2001/0053898 A1 | 12/2001 | Olson et al. | |
| 2003/0233082 A1 | 12/2003 | Kline et al. | |
| 2004/0138633 A1 | 7/2004 | Mishima et al. | |
| 2004/0162536 A1 | 8/2004 | Becker et al. | |
| 2004/0167486 A1 | 8/2004 | Busam et al. | |
| 2005/0070867 A1 | 3/2005 | Beruda et al. | |
| 2005/0101928 A1 | 5/2005 | Beruda et al. | |
| 2005/0177120 A1* | 8/2005 | Olson et al. | 604/361 |
| 2005/0222547 A1 | 10/2005 | Beruda et al. | |
| 2005/0256476 A1 | 11/2005 | Mirle et al. | |
| 2006/0020249 A1 | 1/2006 | Allen | |
| 2006/0114754 A1 | 6/2006 | MacDonald et al. | |
| 2006/0224132 A1 | 10/2006 | Roe et al. | |
| 2006/0229577 A1* | 10/2006 | Roe et al. | 604/361 |
| 2006/0229578 A1* | 10/2006 | Roe et al. | 604/361 |
| 2006/0264858 A1 | 11/2006 | Roe et al. | |
| 2007/0049885 A1* | 3/2007 | Phillips | 604/361 |
| 2007/0185467 A1* | 8/2007 | Klofta et al. | 604/361 |
| 2008/0145945 A1 | 6/2008 | Song | |
| 2008/0147030 A1 | 6/2008 | Nhan et al. | |
| 2008/0147031 A1 | 6/2008 | Long et al. | |

* cited by examiner

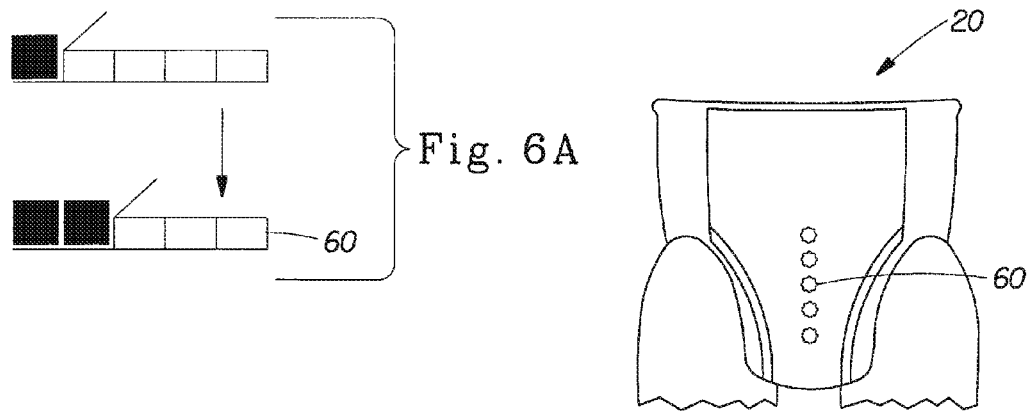
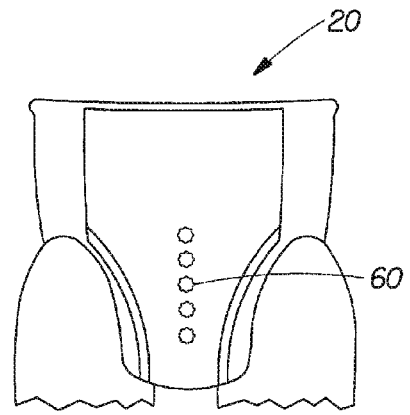
Fig. 6A
Fig. 6B
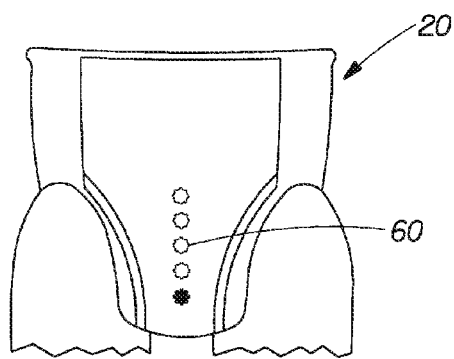
Fig. 6C
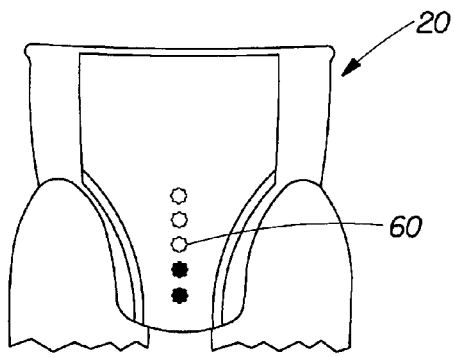
Fig. 6D

ABSORBENT ARTICLE HAVING A POTTY TRAINING READINESS INDICATOR

CROSS REFERENCE TO RELATED APPLICATION

This application claims the benefit under 35 U.S.C. §120 of U.S. Provisional Application No. 60/906,044, filed Mar. 9, 2007.

FIELD OF THE INVENTION

The invention relates to hygienic absorbent articles, such as diapers, pants, adult incontinence articles, and the like including a potty training readiness indicator. More particularly, the invention is directed to an absorbent article having a potty training readiness indicator which indicates when the wearer is ready to be potty trained.

BACKGROUND OF THE INVENTION

Absorbent articles are widely used by infants and incontinent individuals to receive and contain body exudates. There are currently many absorbent articles available which provide a wetness indication feature. However, these wetness indications can do little in the way of providing information regarding when the wearer is ready to be potty trained. Consequently, there is a need for an absorbent article which can provide the caregiver with a signal indicating when the wearer is ready to be potty trained.

SUMMARY OF THE INVENTION

The present invention pertains to an absorbent article having a potty training readiness indicator adapted for wearing about the lower torso of a wearer. The absorbent article comprises a chassis which includes a topsheet, a backsheet which is attached to at least a portion of the topsheet, and an absorbent core disposed between the topsheet and the backsheet.

The potty training readiness indicator is attached to the chassis and comprises an indicating member. The indicating member provides a visible signal when dry and can provide a different signal or disappear when activated; it may also provide no signal when dry and a signal when activated; it may also provide the same signal when dry and wet but further include an expanding moving line; it may also provide a texture signal but not a visual signal.

In one embodiment, there may be an area comprising one or more indicators such that each successive wetness event causes more indicators to be activated.

In one embodiment, the absorbent article is a disposable pull-on diaper or pant having a wearer-facing surface and a garment-facing surface; a longitudinal axis and a lateral axis; and a front waist region; a back waist region, and a crotch region disposed between the front and back waist regions. The front waist region and back waist region are joined to form a waist opening and leg openings.

The disposable pull-on diaper further comprises a topsheet and a backsheet which is attached to at least a portion of the topsheet. The backsheet has an inner surface and an outer surface. An absorbent core is disposed between at least a portion of the topsheet and the backsheet.

A potty training readiness indicator is attached to the inner surface of the backsheet, or the core, topsheet, etc., wherein the potty training readiness indicator comprises indicating members that provide visible signals when dry and different signals when experiencing a wetness event.

BRIEF DESCRIPTION OF THE DRAWINGS

FIGS. 6A-6D show an embodiment of an indicating member.

DETAILED DESCRIPTION OF THE INVENTION

Figure 1:
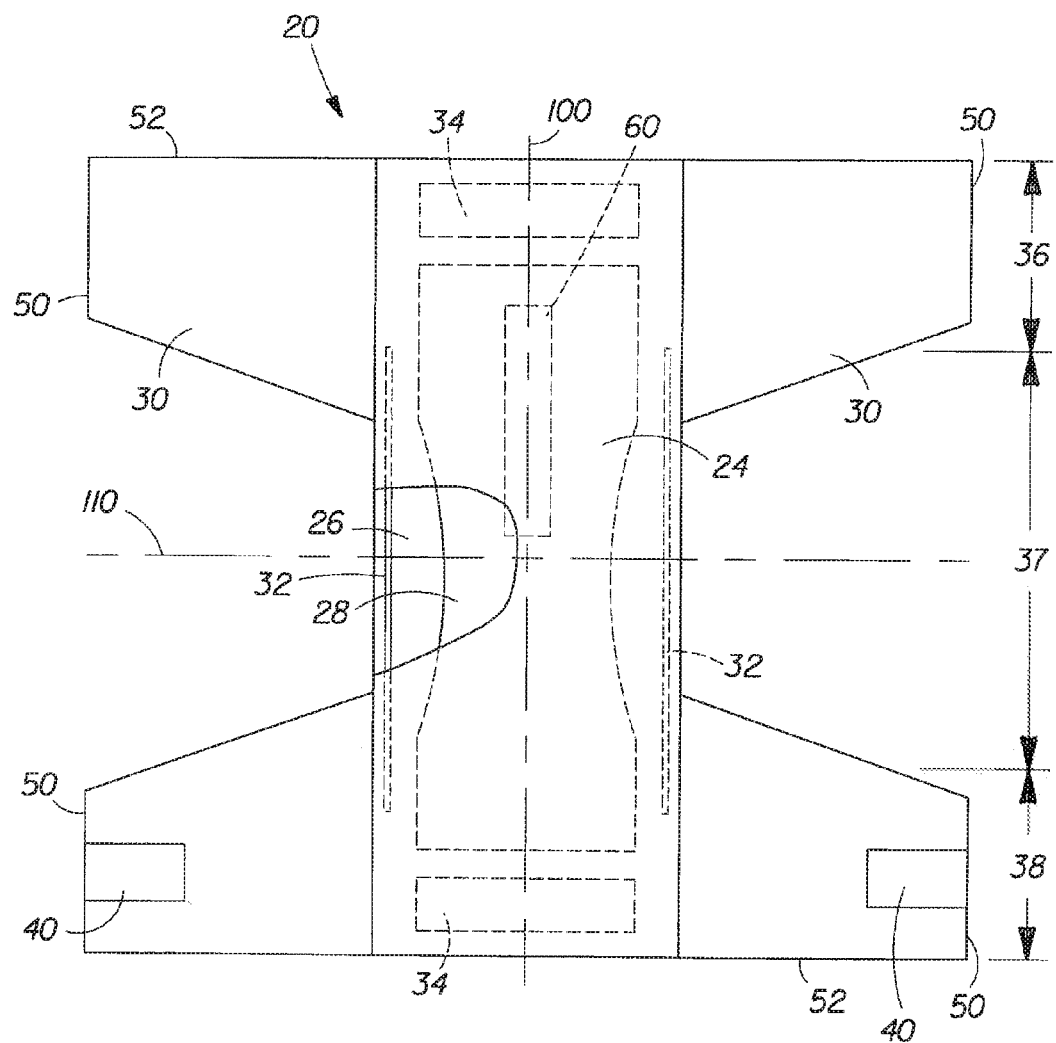
FIG. 1 shows a cut away view of a disposable absorbent article in a flattened, uncontracted, condition, the disposable absorbent article comprising a potty training readiness indicator in accordance with the present invention.

As used herein, the following terms have the following meanings:

As used herein, the term "absorbent article" refers to devices that absorb and contain body exudates and, more specifically, refers to devices that are placed against or in proximity to the body of the wearer to absorb and contain the various exudates discharged from the body. The term "disposable" is used herein to describe absorbent articles that generally are not intended to be laundered or otherwise restored or reused as absorbent articles (i.e., they are intended to be discarded after a single use and, preferably, to be recycled, composted or otherwise discarded in an environmentally compatible manner). The present invention is also applicable to other wearable and absorbent articles such as incontinence briefs, incontinence undergarments, absorbent inserts, diaper holders and liners, feminine hygiene garments, bandages and the like.

As used herein, the term "activate" shall mean to produce an intended action or effect. Any terms conjugated from the term "activate", shall retain the above meaning in the correct conjugated form. In addition, the term "activation" shall refer to the act of producing an intended action or effect.

The term "attached" refers to elements being connected or united by fastening, adhering, bonding, etc. by any method suitable for the elements being attached together and their constituent materials. Many suitable methods for attaching elements together are well-known, including adhesive bonding, pressure bonding, thermal bonding, mechanical fastening, etc. Such attachment methods may be used to attach elements together over a particular area either continuously or intermittently.

As used herein, the term "diaper" refers to an absorbent article generally worn by infants and incontinent persons about the lower torso so as to encircle the waist and legs of the wearer and that is specifically adapted to receive and contain urinary and fecal waste. As used herein, term "diaper" also includes "pants" which is defined below.

As used herein the term "different" when used in the context of the visible signals means any change in color, contrast, tint, shape, size, distance, location, the like, or a combination thereof, of the previous indication to the latter indication.

As used herein, the term "disposed" refers to an element being attached and positioned in a particular place or position in a unitary structure with other elements.

The term "longitudinal" refers to a direction running from a waist edge to an opposing waist edge of the article and generally parallel to the maximum linear dimension of the article. Directions within ±45° of the longitudinal direction are considered to be "longitudinal".

The term "lateral" refers to a direction running from a side edge to an opposing side edge of the article and generally at a right angle to the longitudinal direction and in the same plane as the longitudinal direction. Directions within ±45° of the lateral direction are considered to be "lateral".

The term "orthogonal" refers to a direction that is generally at a right angle to the plane in which the "longitudinal" direction and the "lateral" direction lie. Directions within ±80° of the orthogonal direction are considered to be "orthogonal".

As used herein the term "moisture" includes but is not limited to water, urine, or feces. The moisture can be in a liquid or vapor state.

The terms "pant" or "training pant", as used herein, refer to disposable garments having a waist opening and leg openings designed for infant or adult wearers. A pant may be placed in position on the wearer by inserting the wearer's legs into the leg openings and sliding the pant into position about a wearer's lower torso. A pant may be preformed by any suitable technique including, but not limited to, joining together portions of the article using refastenable and/or non-refastenable bonds (e.g., seam, weld, adhesive, cohesive bond, fastener, etc.). A pant may be preformed anywhere along the circumference of the article (e.g., side fastened, front waist fastened). While the terms "pant" or "pants" are used herein, pants are also commonly referred to as "closed diapers", "prefastened diapers", "pull-on diapers", "training pants" and "diaper-pants". Suitable pants are disclosed in U.S. Pat. No. 5,246,433, issued to Hasse, et al. on Sep. 21, 1993; U.S. Pat. No. 5,569,234, issued to Buell et al. on Oct. 29, 1996; U.S. Pat. No. 6,120,487, issued to Ashton on Sep. 19, 2000; U.S. Pat. No. 6,120,489, issued to Johnson et al. on Sep. 19, 2000; U.S. Pat. No. 4,940,464, issued to Van Gompel et al. on Jul. 10, 1990; U.S. Pat. No. 5,092,861, issued to Nomura et al. on Mar. 3, 1992; U.S. Patent Publication No. 2003/0233082 A1, entitled "Highly Flexible And Low Deformation Fastening Device", filed on Jun. 13, 2002; U.S. Pat. No. 5,897,545, issued to Kline et al. on Apr. 27, 1999; U.S. Pat. No. 5,957,908, issued to Kline et al on Sep. 28, 1999.

The term "obstruct" means to impede or retard the view of an otherwise visible signal.

The terms "permeable" and "impermeable" refer to the penetrability of materials in the context of the intended usage of disposable absorbent articles. Specifically, the term "permeable" refers to a layer or a layered structure having pores or openings that permit liquid water to pass through its thickness in the absence of a forcing pressure. Conversely, the term "impermeable" refers to a layer or a layered structure through the thickness of which liquid water cannot pass in the absence of a forcing pressure. As is well known in the art, a common method for measuring the permeability of the materials typically used in absorbent articles is a hydrostatic pressure test, also called a hydrostatic head test or simply a "hydrohead" test. Suitable well known compendial methods for hydrohead testing are approved by INDA (formerly the International Nonwovens and Disposables Association, now The Association of the Nonwoven Fabrics Industry) and EDANA (European Disposables And Nonwovens Association).

The present invention is a disposable absorbent article comprising a potty training readiness indicator. The potty training readiness indicator can be utilized in a number of different absorbent articles. For example, in a disposable diaper, the potty training readiness indicator can provide a caregiver with useful information concerning the urinary or defecation tendencies of a wearer by counting the number of wetness events, by giving an indication of a wetness event, or by indicating the time to the first wetness event. As another example, in a catamenial product, the potty training readiness indicator can count the number of menses events. Despite the fact that the potty training readiness indicator of the present invention can be incorporated into many different absorbent articles, for the sake of explanation, the present invention will be discussed in the context of a diaper. However, similar embodiments are available in the absorbent articles mentioned heretofore.

The present invention is directed to a potty training readiness indicator that helps a child toilet train more successfully by aiding caregivers in determining when the child is physically ready to be potty trained. Potty training readiness is often indicated by longer periods of the child staying dry. Unlike current training pants which only tell the caregiver if the child has wet the diaper, the potty training readiness indicator may be used to count and display the number of wetness events. The potty training readiness indicator may also be used to measure and display the amount of time the diaper stayed dry after application. Thus, the potty training readiness indicator may be used to measure both the number of urination events and/or the amount of time until the first wetness event and/or provide an indication of a wetness event.

The potty training readiness indicator of the present invention may be measured through various techniques and mechanisms including, but not limited to, a time flow measurement technique, an indicating method, a chromatography method, an encapsulation method, and a pop-up method. The time-flow technique indicates to the caregiver the amount of time that has passed until the first wetness event. The indicating method assists the caregiver in determining the number of times a wetness event has occurred and the amount of urination with each wetness event. The chromatography method, encapsulation method, and pop-up method are all various ways the caregiver can count the number of wetness events. Each of the aforementioned methods are discussed in more detail herein.

FIG. 1 is a plan view of the diaper 20 of the present invention in a flat-out, uncontracted, state with portions of the structure being cut-away to more clearly show the construction of the diaper 20. The portion of the diaper 20 that faces a wearer is oriented towards the viewer. As shown in FIG. 1, the diaper 20 comprises a topsheet 24; a backsheet 26; and an absorbent core 28 that is positioned between at least a portion of the topsheet 24 and the backsheet 26. The absorbent article further comprises side panels 30, elasticized leg cuffs 32, elastic waist features 34, and a fastening system generally designated 40. The diaper 20 has a first waist region 36, a second waist region 38 opposed to the first waist region 36, and a crotch region 37 located between the first waist region 36 and the second waist region 38. The periphery of the diaper 20 is defined by the outer edges of the diaper 20 in which longitudinal edges 50 run generally parallel to a longitudinal centerline 100 of the diaper 20 and end edges 52 run between the longitudinal edges 50 generally parallel to a lateral centerline 110 of the diaper 20.

The diaper 20 further comprises a potty training readiness indicator 60 which can produce a signal indicating when the wearer is ready to be potty trained. For example, the signal can be a visible indication of the number of times the wearer has urinated or the amount of time to the first wetness event. In another example, the signal can be a visible indication of the number of times the wearer has defecated in conjunction with or independently from the number of times the wearer has urinated. Alternative to or in conjunction with the visible indication, the signal can be an audible, tactile, or olfactory, indication, or any combination thereof. For the sake of explanation, visible indications shall be discussed with regard to the embodiments mentioned herein.

The potty training readiness indicator 60 may be located at any point in the absorbent article likely to be contacted by exudates from the wearer. For example, in one embodiment, the potty training readiness indicator 60 can be located in the portion of the article in communication with the urine loading point (i.e., the location in which the urine typically insults the article, such as in the vicinity of the longitudinal centerline 100 of the article in the crotch region 37 of the article). In another embodiment, the potty training readiness indicator 60 may be located remotely from the urine loading point and may comprise an intermediate wicking member which transports moisture from the urine loading point to the potty training readiness indicator 60.

In addition, the potty training readiness indicator 60 may be attached to any component of the article but should be in communication with the urine loading point. For example, the potty training readiness indicator 60 may be attached to the topsheet 24, the absorbent core 28, or the backsheet 26. In one embodiment, the potty training readiness indicator 60 is positioned between the topsheet 24 and the absorbent core 28 and provides a signal that is visible through the topsheet, such as when a waist edge is pulled away from the body of the wearer to enable inspection of the interior of the article. In another embodiment, the potty training readiness indicator 60 may be positioned between the backsheet 26 and the absorbent core 28, such that the signal provided by the potty training readiness indicator can be seen through at least a portion of the backsheet. In yet another embodiment, the potty training readiness indicator 60 may be disposed on the article in such a way that a patch or portion of the article can be pulled away, permanently or temporarily, to expose the indicator such that the signal is visible without the article being removed from the wearer. In yet another embodiment, a separate element which is applied to the absorbent article by the caregiver, such as a diaper insert or other carrier element affixed to an element of the diaper 20 (e.g., via adhesive, a mechanical fastener, friction, etc.) by the caregiver prior to applying the diaper to the wearer may comprise the potty training readiness indicator 60.

Time Flow Method

In the time-flow measurement technique, a timer indicator measures the amount of time from a set start time until a first wetness event. In this mechanism, the start time may be initiated by a specific event by the caregiver or wearer. The initiation of the start time may occur by the caregiver performing an act, including but not limited to, removing a protective strip from the indicator or squeezing the indicator. One example of the time-flow method includes a moving line. Other examples of the time-flow method include, but are not limited to, appearing or disappearing graphics and color changes (i.e. from color to a different color, from color to black or white, from black or white to color, from color to transparent, from transparent to color, from black or white to transparent, from transparent to black or white).

In the moving line example, over time, a colored bar moves from left to right. Examples of commercially available products include MonitorMark™ Time Temperature Indicators from 3M, MN, or Timestrip® Smart Labels from Timestrip Limited, UK. When a wetness event occurs, the movement of the time line may be stopped through a mechanism such as a liquid (e.g. pectin or alginate) that gels upon contact with urine or a component/property of urine such as water, ions, pH, etc. The movement of the time line may also be stopped through the use of a substrate the swells upon contact with urine and thus prevent the moving line liquid from any further flow.

Figure 2A:
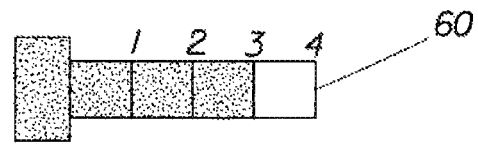
FIGS. 2A-2C show an embodiment of an indicating member.
Figure 2B:
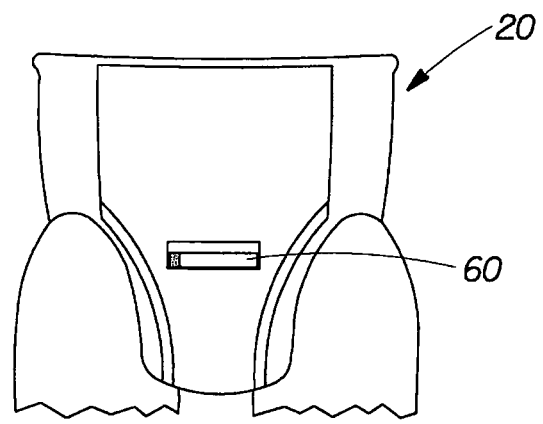
Figure 2C:
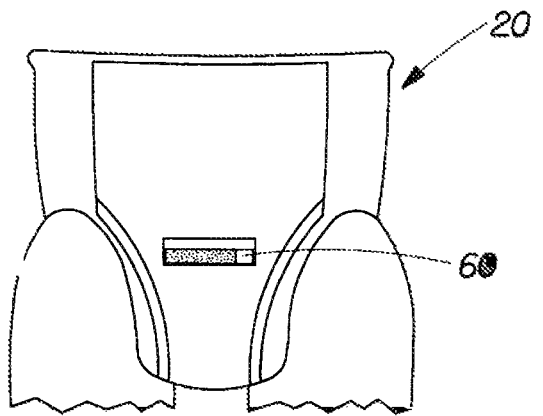

For example, FIGS. 2A-C show a diaper 20 having a time flow method potty training readiness indicator 60. FIG. 2A depicts a moving line indicator; FIG. 2B depicts a moving line figure on a diaper 20 indicating that the time is at "0", or the start time; FIG. 2C shows a moving line figure on a diaper 20 indicating that the time is some time later than "0".

Indicating Method

A mechanism for measuring the number of wetness events includes an indicating method. In this mechanism, a first area can change appearance (color change, appearing/disappearing graphics) with a first event. A second area, which may or may not overlap the first area depending on the position of the child, can change appearance with a second event. The exact size of the area is dependent on the volume of urine, the amount and nature of the absorbing material, and position of the child. Each area may include one or more indicating members. Thus, each successive wetness event causes more indicators to be activated. As one or more wetness indicators are activated with the first wetness event, and the amount of area of the wetness indicators activated is determined by the volume of urine and the position of the child. The second wetness event activates additional wetness indicators after the second wetness event, and so on. This method may involve a process whereby the parent checks the product over time to see if more areas have changed to get an indication of the number and size of urination events.

Figure 3A:
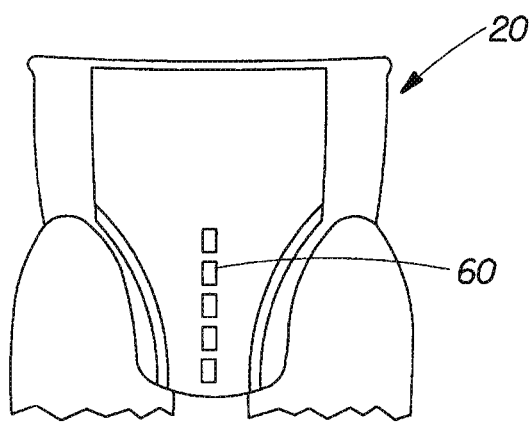
FIGS. 3A-3C show an embodiment of an indicating member.
Figure 3B:
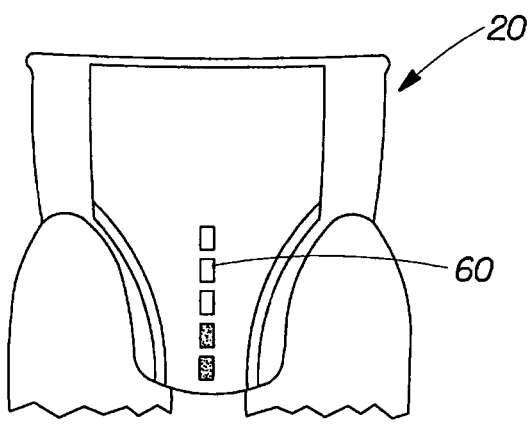
Figure 3C:
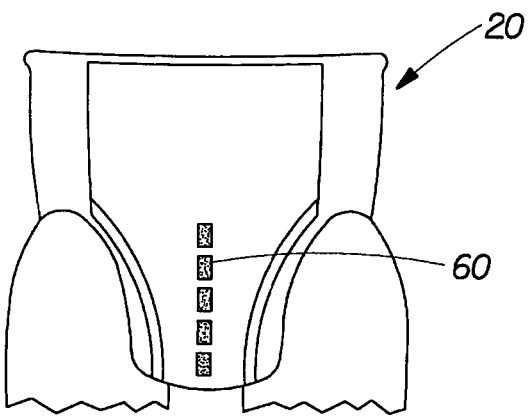

For example, FIGS. 3A-C show a diaper 20 having an indicating method potty training readiness indicator 60. FIG. 3A is an indicating method indicator on a diaper 20 indicating that the time is at "0", or the start time; FIG. 3B shows an indicating method indicator on a diaper 20 indicating that at least one wetness event has occurred; FIG. 3C shows an indicating method indicator on diaper 20 indicating that at least two or more wetness events have occurred.

Chromatography Method

A mechanism for measuring the number of urination events includes a chromatography method. One example of the chromatography method is the display of a new ring for each wetness event. The total number of rings equals the total number of wetness events. This technology is based upon typical dyes and chromatography paper. The mechanism utilizes technology to trap the dye in the substrate after each urination event in order to produce the multiple rings. Other examples of the chromatography method include, but are not limited to, color changes for each wetness event or appearing graphics.

Figure 4A:
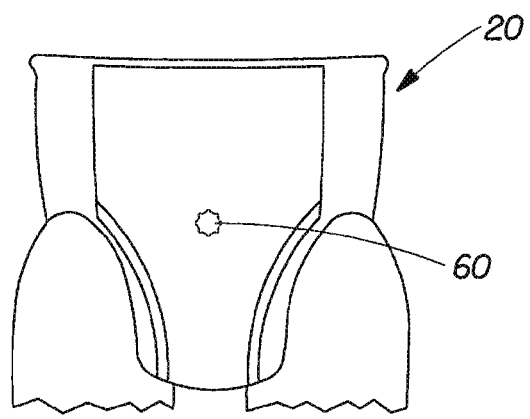
FIGS. 4A-4C show an embodiment of an indicating member.
Figure 4B:
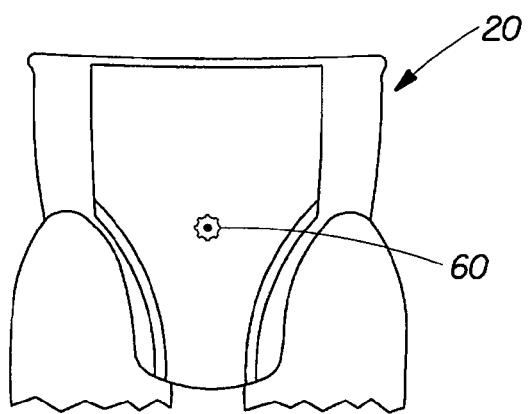
Figure 4C:
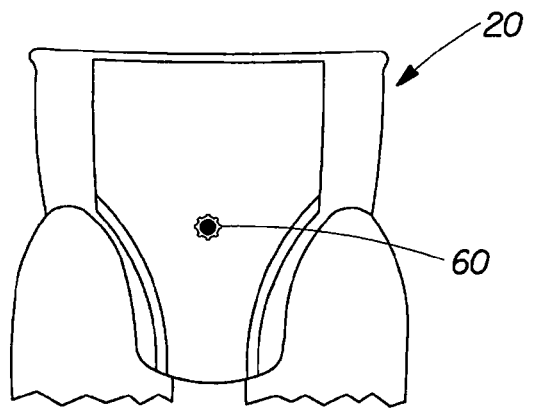

For example, FIGS. 4A-C show a diaper 20 having a chromatography method potty training readiness indicator 60. FIG. 4A depicts a chromatography method indicator on a diaper 20 when zero (0) wetness events have occurred; FIG. 4B shows a chromatography method indicator on a diaper 20 when one (1) wetness event has occurred; FIG. 4C shows a chromatography method indicator on a diaper 20 when two (2) wetness events have occurred.

Encapsulation Method

Another mechanism for measuring the number of urination events includes an encapsulation method. In one example of the encapsulation method, the indicator may display a different color symbol for each urination event. For example, the first wetness indicator may start out one color, and a first wetness event turns the first wetness indicator a different color, and each additional wetness event may turn the second wetness indicator a second different color. In another embodiment of this mechanism, there may be only one wetness indicator and each wetness event may turn the same indicator a different color. Further, in another embodiment, there may be more than one indicator where the first indicator changes color with the first wetness event, and the second indicator changes color with the second wetness event. In another embodiment, the indicator may not change color with each wetness event but may provide a different signal such as an increase in size of the indicator. In each of the aforementioned examples, the signal may be achieved by mechanisms other than a color change. These mechanisms may include, but are not limited to, a growing indicator or a changing graphic.

The encapsulation method technology is based upon encapsulating multiple layers of dyes in protective layers that degrades slowly over time after exposure to a wetness event. Thus, only one color of dye can be released with each urination event.

Figure 5A:
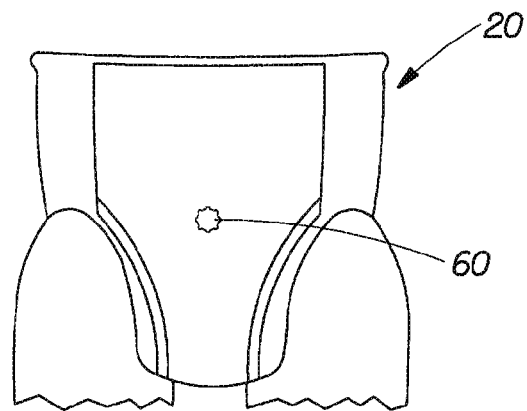
FIGS. 5A-5C show an embodiment of an indicating member.
Figure 5B:
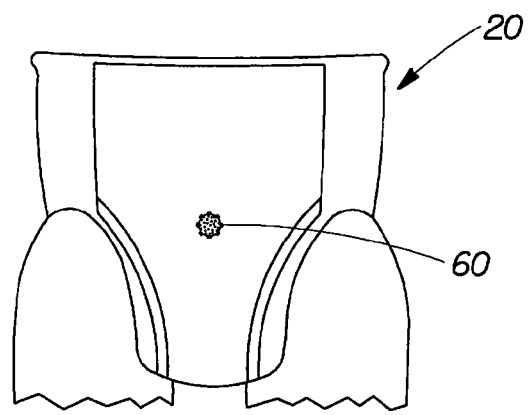
Figure 5C:
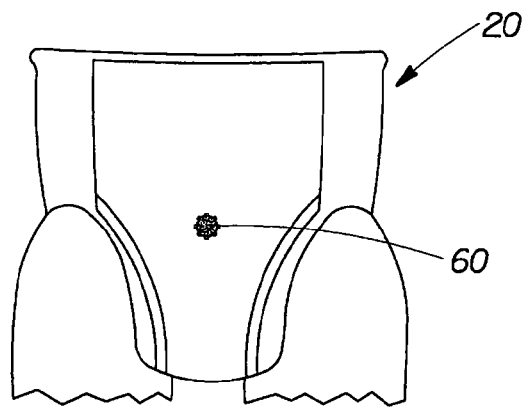

For example, FIGS. 5A-C show a diaper 20 having an encapsulation method potty training readiness indicator 60. FIG. 5A depicts an encapsulation method indicator on a diaper 20 when zero (0) wetness events have occurred; FIG. 5B shows an encapsulation method indicator on a diaper 20 when one (1) wetness event has occurred;

FIG. 5C shows an encapsulation method indicator on a diaper 20 when two (2) or more wetness events have occurred.

Pop-Up Method

In this method, wetness events may cause indicators to swell and/or pop-up, indicating that a wetness event has occurred. For example, a first wetness event may cause the first indicator to swell or pop-up against the top or backsheet, providing a visual or tactile indication of the first wetness event. Likewise, the first wetness event could cause the first indicator to move away from the top or backsheet, acting like a disappearing graphic. After the first indicator swells and/or pops up, there may be an event that will lead to exposing the second wetness indicator, which will allow for the activation of the second wetness indicator. This event may include breaking a fragile protective seal around the second indicator. The second wetness event thus activates the second indicator and exposes the third indicator, etc.

For example, FIGS. 6A-D show a diaper 20 having a pop-up method potty training readiness indicator 60. FIG. 6A depicts a pop-up indicator; FIG. 6B depicts a pop-up method indicator on a diaper 20 when zero (0) wetness events have occurred;

FIG. 6C shows a pop-up method indicator on a diaper 20 when one (1) wetness event has occurred; FIG. 6D shows a pop-up method indicator on a diaper 20 when two (2) wetness events have occurred.

Indicator Technologies

The aforementioned potty training readiness indicator techniques and mechanisms may utilize various technologies. Many of these technologies are described in U.S. patent application Ser. Nos. 11/100,653 and 11/400,633.

Figure 7:
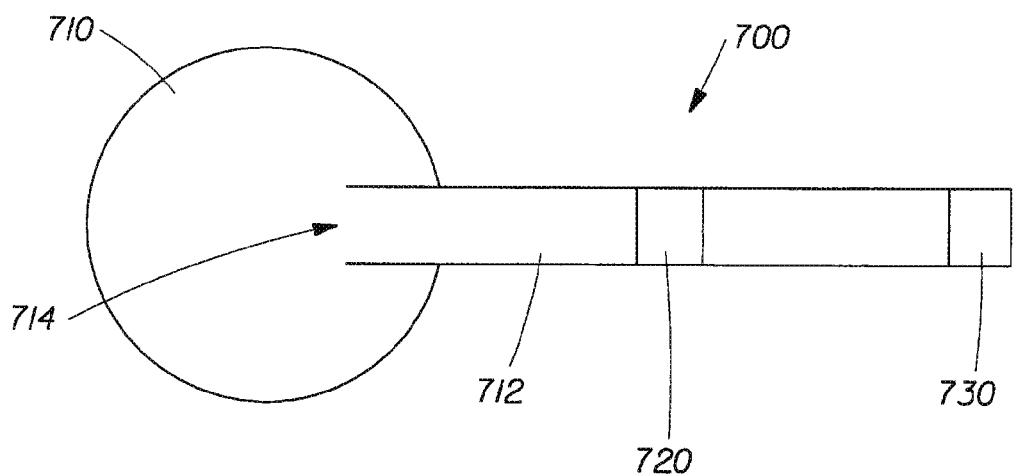
FIG. 7 shows an embodiment of the potty training readiness indicator of FIG. 1 which includes a plurality of indicating members.

For example, FIG. 7 shows a wicking member 712 may be utilized in a potty training readiness indicator. An indicating apparatus 700 may comprise the wicking member 712, a first transferring member 720 and a second transferring member 730. Upon a first wetness event, a moisture source 710 is created thereby supplying moisture to an opening 714 in the wicking member 712. Moisture from the moisture source 710 can enter the opening 714 in the wicking member 712. The first transferring member 720 is in communication with the wicking member 712 such that the moisture can wick through the wicking member 712 to the first transferring member 720. When the moisture in the wicking member 712 reaches the first transferring member 720, the moisture activates the first transferring member 720.

The activation of the first transferring member 720 provides a visible and/or tactile indication of the first wetness event. In addition, the first transferring member 720 may absorb moisture from the moisture source 710. By absorbing moisture from the moisture source 710, the first transferring member 720 can preclude moisture from prematurely activating the second transferring member 730. The first transferring member 720 can be sized such that it is fully saturated upon absorbing all of the moisture from the moisture source 710. In addition, the first transferring member 720 may be sized such that the first transferring member 720 absorbs the moisture from within the wicking member 712.

On a subsequent wetness event, the moisture source 710 is re-supplied with moisture. Moisture is provided by the moisture source 710, thereby wicking through the wicking member 712. Additionally, the moisture can be transferred through the first transferring member 720 to the second transferring member 730. The second transferring member 730 is in communication with the wicking member 712 such that moisture transferred from the first transferring member 720 wicks toward the second transferring member 730. Moisture from the second wetness event activates the second transferring member 730, thereby causing the second transferring member 730 to provide a visible indication of the second wetness event.

Alternatively, the first transferring member 720 may be sized such that moisture remains in the wicking member 712 even after moisture from the moisture source 710 has been absorbed. Due to the meniscus effect, moisture within the wicking member 712 can remain even after the moisture source 710 is depleted. On a subsequent wetness event, the moisture source 710 is replenished such that the moisture within the wicking member 712 can advance to the second transferring member 730.

The first and second transferring members may comprise a surfactant, an emulsifier, waxes, AGM, a sponge, a clay, a hydrogel, fluid stable aggregates, and high surface area polymeric foams, and mixtures thereof. Suitable high surface area foams for use in the present invention are further described in U.S. Pat. Nos. 5,387,207; 5,650,222; 6,013,589; and 6,083,211. The first transferring member 720 and the second transferring member 730 may comprise a reactive element or reactive layer, or any components of an indicating member, as described heretofore. The reactive element can allow the first transferring member 720 and the second transferring member 730 to provide a visible indication of a wetness event. For example, the transferring members 720, 730 may comprise a pH indicator which changes color after being contacted by the moisture.

Suitable AGM's are further described in U.S. patent application Ser. No. 10/950,011 entitled "Absorbent Articles Comprising Superabsorbent Polymer Having a Substantially Non-covalently Bonded Surface Coating" filed in the name of Beruda, et al. on Sep. 24, 2004, in U.S. patent application Ser. No. 10/941,672, entitled "Absorbent Articles Comprising Fluid Acquisition Zones with Superabsorbent" filed in the name of Beruda, et al. on Sep. 15, 2004 and in JP 2004-105118, entitled "An Aqueous-Liquid-Absorbing Agent and Its Production Process", filed in the name of Nippon Shokubai Co. Ltd. on Mar. 31, 2004.

The wicking member 712 may comprise a single channel or a plurality of channels. The wicking member 712 may comprise a capillary tube, a plurality of capillary tubes, or a wicking strip. The single tube or the plurality of tubes may be vapor impermeable. The first transferring member 720 and second transferring member 730 may be positioned in the wicking member 712. Alternatively, the wicking member 712 may comprise a first portion which extends from the moisture source 710 to the first transferring member 720 and a second portion which extends from the first transferring member 720 to the second transferring member 730.

In another embodiment, the first transferring member 720 may be selected such that it absorbs moisture from the moisture source 710 and expands in size such that excess moisture is unable to pass through the wicking member 712 to the second transferring member 730. Subsequently, the first transferring member 720 may desorb the absorbed moisture, thereby drying out. Upon drying out, the first transferring member 720 could form fissures therein allowing moisture to pass therethrough upon subsequent rewetting. Therefore, upon a second wetness event, moisture may pass through the fissures in the first transferring member 720 to the second transferring member 730, thereby actuating the same.

For this embodiment, the wicking member 712 may comprise a vapor permeable tube or plurality of tubes. The vapor permeability of the wicking member 712 could allow the first transferring member 720 to desorb the absorbed moisture from the first wetness event. Alternatively, the wicking member 712 may be coated with a hydrophobic coating to prevent moisture from other areas of the absorbent article from inadvertently wetting the wicking member 712 to cause further flow along the wicking member 712.

With regard to this embodiment, the wicking member 712 can be a vapor permeable material which is not soluble in water. Suitable examples are micro-porous films or a vapor permeable barrier layers as further described in U.S. application Ser. No. 10/844,182, entitled, "Breathable Absorbent Articles and Composites Comprising A Vapor Permeable, Liquid Barrier Layer", filed on May 12, 2004. The wicking member 712 may comprise any vapor permeable material known in the art which is operable in this embodiment.

With regard to this embodiment, suitable material for the first transferring member 720 and the second transferring member 730 are any material known in the art which absorbs moisture and increases in permeability when it dries out which would be operable in this embodiment. The first transferring member 720 and the second transferring member 730 may also comprise clay as discussed previously. Note that additional transferring members can be added to the embodiments discussed above.

In another embodiment, the first transferring member 720 may contain a pH indicator or indicating component which changes color after being contacted by moisture. In this embodiment, the first transferring member 720 can preclude further urine migration along the wicking member 712 and can slowly dissolve after being contacted by urine from the first urination event. For example, the first transferring member 720 may be an ethoxylated alcohol surfactant of the optimum lipophilic/hydrophilic ratio such that it has the ability to stop the wicking of moisture during the first wetness event. However, after the first wetness event, the first transferring member 720 can completely dissolve, thereby preparing the wicking member 712 for moisture from the second wetness event.

In another embodiment, the first transferring member 720 may be selected such that it absorbs moisture from the moisture source 710 and effervesces in an optimum time frame to cause both a change in pH and break down of the 720 transferring member. Acids such as citric acid and the like can be used to react with sodium carbonate or sodium bicarbonate and mixtures thereof to cause the formation of carbon dioxide gas. The carbon dioxide gas is responsible for the fizzing action and can be used to break up the first transferring member 720 if properly formulated within the matrix of the material of the first transferring member 720. In this embodiment, an acid such as citric acid could also be impregnated onto the wicking member 712. Upon contact with moisture from a wetness event, which flows along the wicking member 712, the citric acid could dissolve and lower the pH of the moisture as it flowed toward the first transferring member 720. As a consequence of containing either sodium carbonate or sodium bicarbonate (or mixtures thereof or other appropriate effervescent agents) along with suitable solubilization agents (emulsifiers, surfactants, hydrophilic solvents), the effervescence reaction would commence as the low pH moisture contacted the first transferring member 720. The resulting pH change within the first transferring member 720 could be used to cause a visible indication via a pH indicator contained in the first transferring member 720. In addition, the gas production reaction could be used to break down the structure of the first transferring member 720 such that moisture from a second wetness event could wick to the second transferring member 730.

In another embodiment, the wicking member 712 may be coated with a color changing agent such as a pH indicator or indicating component as described herein. Alternatively, the wicking member 712 may be coated with an indicating composition such that after contact with moisture, a color change would occur. Thus, during the first urination event, a visible indication along the wicking member 712 could occur up to the point of this first transferring member 720 which can be configured to stop the flow of moisture during the time of the first urination event. Also, as discussed above, the first transferring member 720 can be configured to dissolve after the first wetness event. Similarly, during a second wetness event, the wicking member 712, between the first transferring member 720 and the second transferring member 730, can exhibit a visible indication of the second wetness event.

In another embodiment, numbers might be permanently printed on the backsheet or topsheet next to the first transferring member 720 and second transferring member 730 such that a numerical indication of a wetness event is visibly indicated. For example, a designation, #1, can be printed on the backsheet of the absorbent article adjacent the first transferring member 720 such that upon the first wetness event, the designation, #1, is highlighted to a caregiver. Similarly, upon a second wetness event, a designation, #2, which can be associated with the second transferring member 730, can be highlighted to a caregiver.

Additionally, the designations, #1 and #2 can be equally applied to any of the embodiments discussed herein. The designations may further include #3 and #4 which are associated with third and fourth indicating member as discussed herein. The designations may be printed on the article. For example, the designations may be printed on the topsheet, the backsheet, the core, or combinations thereof. Additionally, the designations may be printed on the indicating members themselves such that the designation is visibly indicated to a caregiver upon its corresponding wetness event The indicating members may comprise multiple layers. For example, the multiple layers may be substantially concentric, substantially disc shaped, or in many different shapes such as a generally annular shape or in a generally spherical shape (if spherical, then a cross section through the center of each sphere is shown). Any shape known in the art can be used for the layers.

Figure 8A:
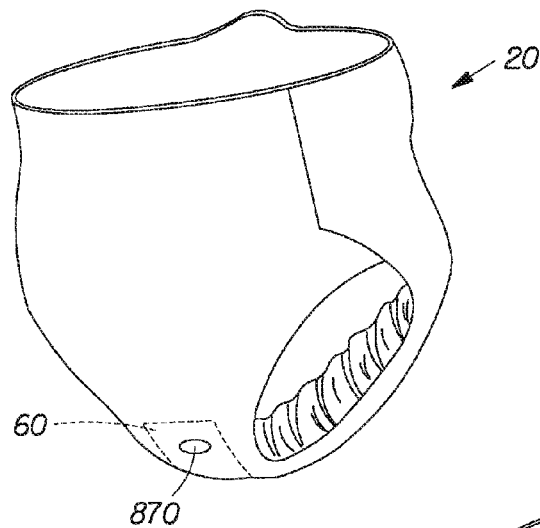
FIGS. 8A-8C show different embodiments of the potty training readiness indicator of FIG. 1 in a pant type absorbent article.
Figure 8B:
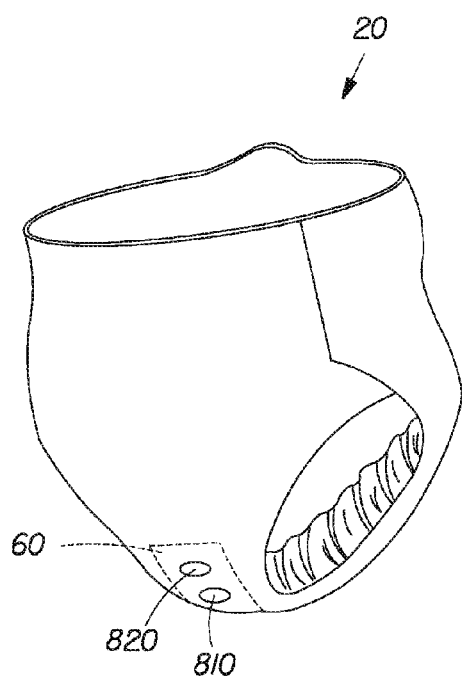
Figure 8C:
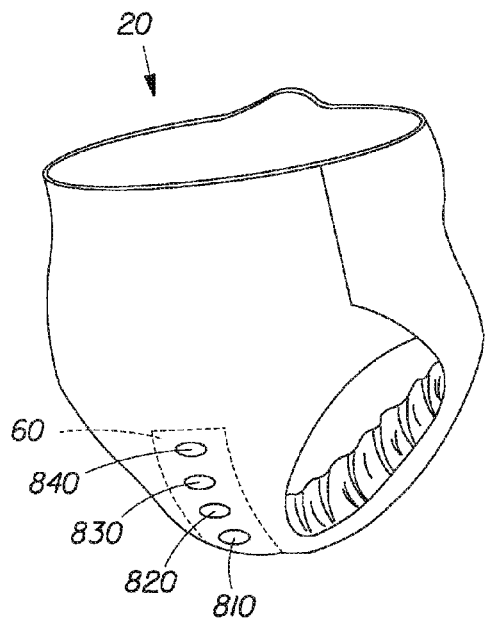

As shown in FIG. 8A, the potty training readiness indicator 60 may comprise a single indicating member 870. FIGS. 8B and 8C demonstrate that the present invention may include a plurality of wetness indicating members or areas that may comprise a first indicating member/area wherein a first wetness event activates the first indicating member/area 810 thereby causing the first indicating member/area 810 to provide a first signal. In some embodiments, the first signal can be a visible indication, i.e. appearing upon the first wetness event. In some embodiments, the first signal can be an obstructed indication, i.e. becoming obstructed upon a first wetness event. As an example, the first signal can be a color change or appearance on the backsheet of the article. Subsequently, a second wetness event may activate the second indicating member/area 820 thereby causing the second indicating member/area 820 to provide a second signal. The second signal can be configured similarly to the first signal. Namely, upon a second wetness event the second signal can appear or become obstructed. For example, the second signal may include a separate visible indication from the first visible indication, or the second visible indication may change the shape or the size or the color of the first signal.

The potty training readiness indicator may further comprise a third indicating member 830, a fourth indicating member 840, and so on, in addition to the first indicating member 810 and the second indicating member 820.

Figure 9A:
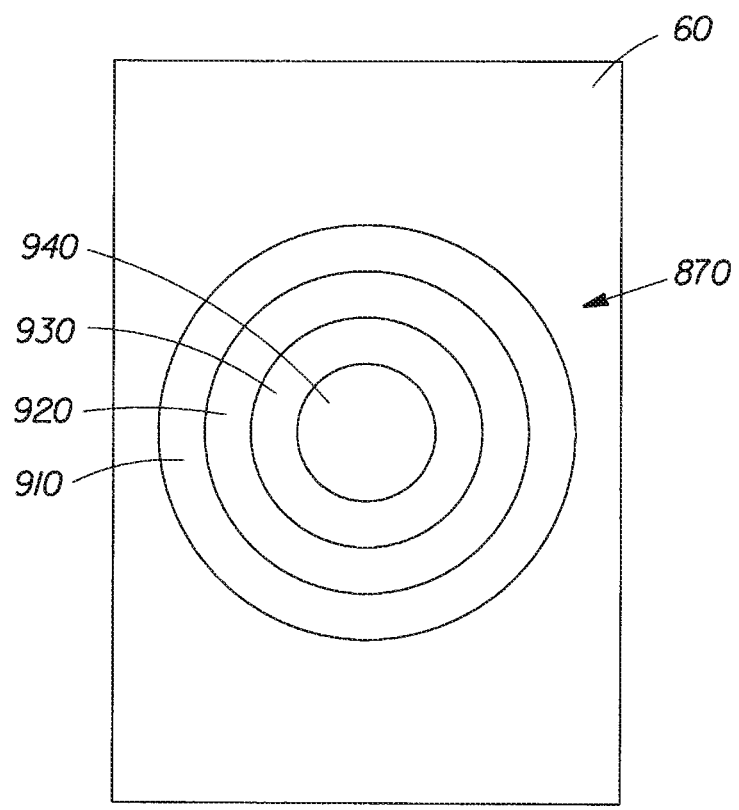
FIG. 9A shows an embodiment of an indicating member of FIG. 8A.
Figure 9B:
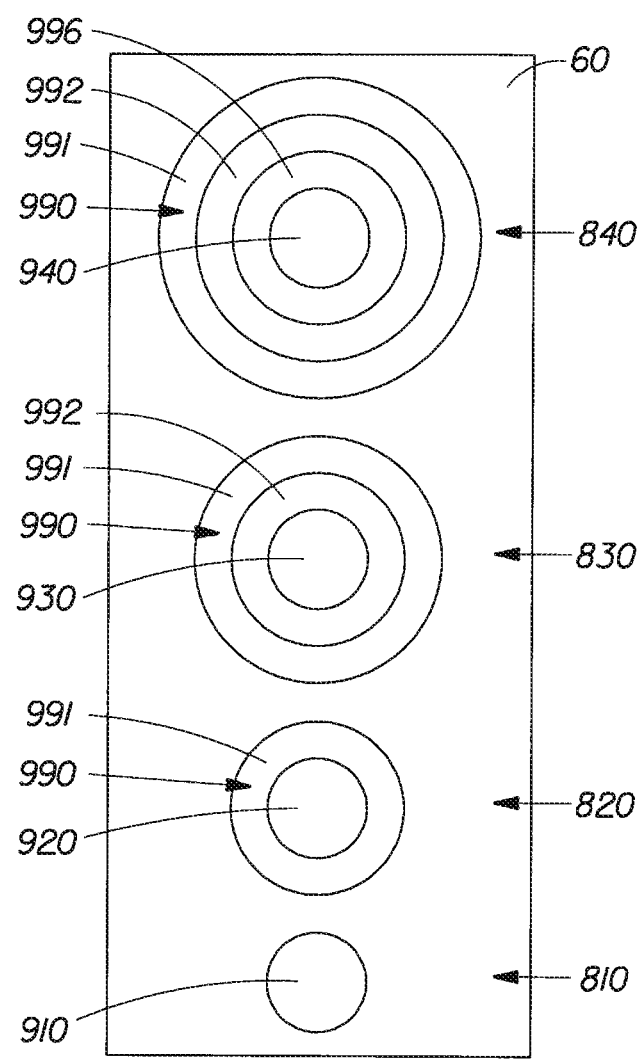
FIG. 9B shows another embodiment of the plurality of indicating member of FIG. 8C.

As shown in FIGS. 9A and 9B, the single indicating member 870, or any of the plurality of wetness indicating members 810, 820, 830, 840, etc., may comprise a first reactive element 910 and a second reactive element 920 surrounded by the first reactive element 910. The single indicating member 870 may further comprise a third reactive element 930 and a fourth reactive element 940 wherein the third reactive element 930 is surrounded by the second reactive element 920 and the fourth reactive element 940 is surrounded by the third reactive element 930.

The indicating members may comprise reactive elements that are completely or partially encapsulated by non-reactive portions or non-reactive elements 990. Note that if the indicating members comprise counter-acting elements, then the first reactive element 910 may completely or partially encapsulate the counter-acting element corresponding thereto. Partial encapsulation of the reactive element, reactive layer, or counter-acting element, may or may not provide sufficient protection from premature activation by moisture.

In another embodiment, the first, second, third, and fourth indicating members may be positioned adjacent the inner surface of the backsheet. The reactive elements 920, 930, and 940, are exposed on their backsheet-facing surfaces; however, they are not exposed on their wearer-facing surfaces. For example, the first non-reactive portion 991 of the second indicating member 820 may cover the second reactive element 920 such that moisture from either the orthogonal direction or the longitudinal direction does not prematurely activate the second reactive element 920. Similarly, the non-reactive elements or portion 992, 996, for the third and the fourth indicating members 830 and 840, respectively, may cover the third and fourth reactive elements 930 and 940, respectively. The coverage provided by the non-reactive elements or portions may preclude premature activation of the reactive elements. Therefore, moisture from a first wetness event can contact the second, third, or fourth indicating members 820, 830, and 840, from the orthogonal direction, the longitudinal direction, or the lateral direction, without prematurely activating the reactive elements of the second, third, and fourth indicating members 820, 830, and 840.

Note that in the embodiments discussed heretofore, the moisture provided by the wearer can dissolve the non-reactive members and non-reactive areas where present. For example, the potty training readiness indicator can be exposed to an area in an absorbent article which retains moisture from a moisture source for five minutes. The non-reactive elements and non-reactive areas of this example can be selected such that they do not dissolve in less than ten minutes. In this manner, the potty training readiness indicator may distinguish between a first wetness event and a second wetness event.

Suitable non-reactive elements, non-reactive portions, barrier layers, and protective layers, may include various materials such as surfactants and emulsifiers which will dissolve at different rates depending upon the relative proportion of hydrophilic to hydrophobic properties of the given molecule. For example, a solid polyethylene glycol of molecular weight of around 1000 will be very soluble in urine and dissolve quickly. Conversely, a solid hydrophobic paraffin or microcrystalline wax will have virtually no solubility in urine. In addition, various chemical classes of molecules can be designed to solubilize at desired rates. For instance, the fatty alcohol known as stearyl alcohol would dissolve very slowly in urine due to the molecule being dominated by the hydrophobic C18 alkyl chain. Although the hydroxyl group in stearyl alcohol contributes some hydrophilicity to the molecule, the molecular structure is dominated by the hydrophobic alkyl chain. To enhance its solubility in urine, the hydroxyl group of the stearyl alcohol could be ethoxylated to varying degrees to increase its solubility in urine. Generally, as more ethoxylate is reacted onto the C18 alkyl chain of the stearyl alcohol, the molecule becomes more soluble in urine. Thus, the solubility of the stearyl alcohol could be tailored to dissolve at different rates depending on the degree of ethoxylation. Uniqema (Wilmington, Del. U.S.A.) makes various ethoxylated fatty alcohols which would dissolve at different rates in urine depending on the alkyl chain length and degree of ethoxylation. Not to be limited by only ethoxylated alcohols, there are many other surfactants, emulsifiers, general classes of molecules, and combinations thereof, which can be configured to dissolve at the desired and optimized rate after contacting urine.

Non dissolving non-reactive elements, non-reactive portions, barrier layers, and protective layers, may include, but are not limited to, non-polar materials as waxes, polyethylenes, high molecular weight fatty alcohols and fatty acids, and other hydrophobic materials. Solids of generally high solubility in urine would be those polar materials such as ethoxylated alcohols, polyethylene glycols, polyvinyl alcohol, water soluble inorganic salts, and other hydrophilic materials and other hydrophilic materials which include but are not limited to emulsifiers, solubilizers, surfactants, and polymers. Any suitable hydrophilic material operable in the embodiments discussed herein may be utilized in the present invention.

Alternatively, the non-reactive elements, non-reactive portions, barrier layers, and protective layers, contacted by moisture from wetness events could be selected such that they absorb moisture from the first wetness event and subsequently desorb the moisture thereby drying out. Upon drying out, the non-reactive members and areas could form fissures, e.g. cracks, crevices, openings, rifts, splits, etc., therein, such that moisture from future wetness events can pass through the fissures. Thus, on subsequent wetness events, moisture could reach a reactive element, non-reactive element, or non-reactive area through the fissures formed in the previous non-reactive element or non-reactive area. As discussed herein, the opposite reaction may also be used wherein the non-reactive element could absorb moisture from the first wetness event, expand and thus break, allowing moisture from future wetness events to reach the next reactive element.

A suitable material for use as the non-reactive elements, non-reactive portions, barrier layers, and protective layers, which form fissures after drying out, is clay. Clays are a class of materials known to shrink and swell depending upon the moisture content within its structure. In fact, at very dry conditions, clays can crack and fissure in order to create capillary pathways for urine flow. The montmorillonite clays are known to swell and contract dramatically depending upon the water content within their matrix. Another novel material that swells and contracts as a function of pH or calcium ion concentrations are forisomes. These are protein aggregates that are found in plants to protect leaves from nutrient loss. Cross linked polyacrylates are also suitable for use in the non-reactive elements, non-reactive portions, barrier layers, and protective layers. Further, AGM materials are useful in the present invention, as they may swell and burst.

The non-reactive elements, non-reactive portions, barrier layers, and protective layers, may need to be specifically sized such that their capacity to preclude premature activation of the reactive elements is not exceeded. For example, the non-reactive elements may be sized in accordance with data concerning the average urinary or fecal discharge of the wearer. Optionally, the indicating members may be strategically placed within the article such that moisture in excess of the non-reactive elements or areas capacity is absorbed by the absorbent core.

Embodiments of the present invention allow for the cumulative counting of wetness events. Specifically, a portion of the first indicating member 810 can provide a visible indication of a wetness event and maintain that visible indication throughout subsequent wetness events. Similarly, the second, third, and fourth indicating members 820, 830, and 840, can also maintain their visible indications for subsequent wetness events. However, the indicating members can be configured such that a visible indication from a prior wetness event is affected on a subsequent wetness event.

Embodiments of the present invention wherein the indicating members can be configured such that a visible indication from a prior wetness event is affected on a subsequent wetness event may occur in many different ways. For example, a subsequent wetness event may affect the previous visible indication by causing the previous visible indication to disappear or by masking, or covering the previous visible indication or by obstructing the previous visible indication. In another example, a subsequent wetness event may affect a previous visible indication by causing a change in color, contrast, tint, shape, size, or a combination thereof, of the previous visible indication.

Each of the indicating members in this embodiment comprises a reactive element, i.e. first reactive element 910, second reactive element 920, third reactive element 930, and a fourth reactive element 940. However, the first, second, and third indicating members 810, 820, and 830 may each further comprise counter-acting elements. Specifically, the first indicating member 810 may further comprise a first counter-acting element, the second indicating member 820 may further comprise a second counter-acting element, and the third indicating member may comprise a third counter-acting element.

The operation of the indicating members in this embodiment is similar to that discussed above. As discussed previously, moisture from a first wetness event can activate the first reactive element 910 such that a visible indication of the first wetness event is provided by the first reactive element 910. However, moisture from a second wetness event can activate the first counter-acting element thereby causing the first counter-acting element to affect the visible indication provided by the first reactive area 910. Note that the first counter-acting element can be selected such that subsequent wetness events, beyond the second wetness event, have no effect on the first counter-acting element.

Similarly, moisture from a third wetness event can activate the second counter-acting element, thereby causing the second counter-acting element to affect the visible indication provided by the second reactive element 920. Similar to the first counter-acting element, the second counter-acting element can be configured such that subsequent wetness events, beyond the third wetness event, have no effect on the second counter-acting element.

Moisture from a fourth wetness event can activate the third counter-acting element, thereby causing the third counter-acting element to affect the visible indication provided by the third reactive element 930. Similar to the first counter-acting element and the second counter-acting element, the third counter-acting element can be configured such that subsequent wetness events beyond the fourth wetness event have no effect on the third counter-acting element.

Another embodiment of the present invention wherein the visible indications of previous wetness events can be affected on subsequent wetness events includes a first indicating member 810 that may comprise a first protective layer, a first reactive layer, a second protective layer, and a second reactive layer. Moisture from a first wetness event may transfer through the first protective layer and activate the first reactive layer such that a visible indication is provided to indicate the first wetness event. The second protective layer can be positioned such that moisture from the first wetness event does not activate the second reactive layer. However, moisture from a second wetness event may transfer through the second protective layer and activate the second reactive layer. The activation of the second reactive layer can alter the visible indication provided by the first reactive layer as described above.

Additional protective layers may be added to the subsequent indicating members as required. Alternatively, an individual protective layer for a subsequent indicating member can be selected such that it precludes activation of a reactive layer from the moisture of multiple wetness events.

The indicating members of the present invention should be configured such that the correct reactive element, reactive layer, or counter-acting element is activated by moisture from a specific wetness event. For example, the reactive element of the second indicating member should be activated by moisture from a second wetness event. Thus, the second indicating member should be configured such that moisture from a first wetness event does not activate the reactive element of the second indicating member. There are many ways to configure the indicating members such that their respective reactive elements, reactive layers, or counter-acting elements are activated by moisture from the proper wetness event.

Embodiments are contemplated utilizing the expansion of the transferring members to produce a visible indication, such as an indicator popping up. For example, a potty training readiness indicator, in some embodiments, may comprise a first indicating member which is visible through the backsheet of a disposable absorbent article when dry. The potty training readiness indicator may further comprise a first expanding member disposed adjacent to the first indicating member. In some embodiments, the first expanding member can surround the first indicating member.

Upon a first wetness event, the first expanding member can expand such that the first indicating member is moved away from the backsheet of the disposable absorbent article. In moving away from the backsheet of the disposable absorbent article, the first indicating member becomes less visible through the backsheet of the disposable article. A disposable absorbent article may comprise a plurality of indicating members and expanding members. The indicating member and expanding members can be configured as described above and such that upon subsequent wetness events, the expanding members expand such that the indicating members are no longer visible through the backsheet of the disposable absorbent article.

Embodiments are contemplated where the first indicating member is not visible when the disposable absorbent article is in a dry state. Instead, upon a wetness event, the first expanding member can expand such that the first indicating member becomes visible through the backsheet.

Figure 10A:
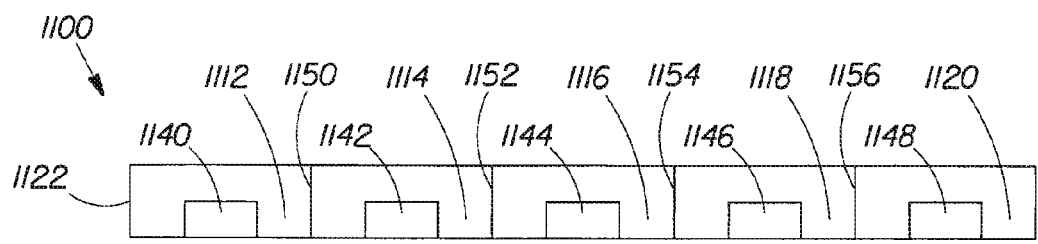
FIG. 10A is an elevation view showing another embodiment of a potty training readiness indicator.
Figure 10B:
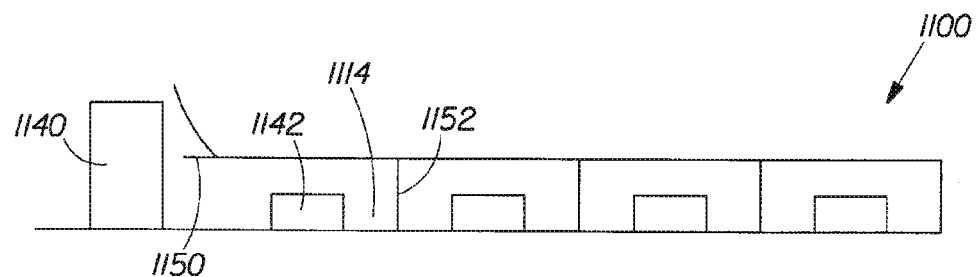
FIGS. 10B and 10C are elevation views showing the potty training readiness indicator of FIG. 10A after a first wetness event and second wetness event, respectively.
Figure 10C:
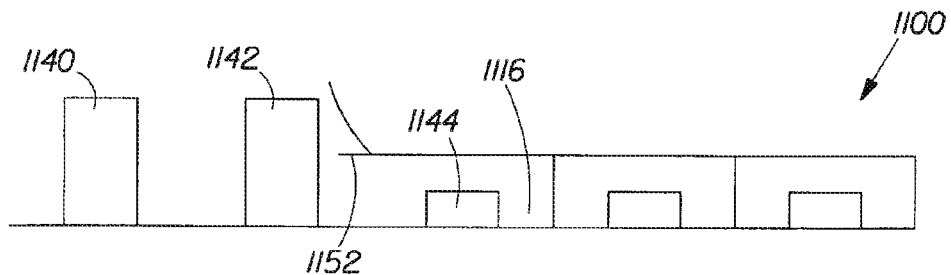

As show in FIG. 10, potty training readiness indicator 1100, in some embodiments, may comprise multiple indication cells 1112, 1114, 1116, 1118, and 1120. In some embodiments, expanding indicators are disposed within each indication cell. The expanding indicators are denoted 1140, 1142, 1144, 1146, and 1148. Between each indication cell, there can be a separation wall. For example, as shown, a separation wall 1150 can be between the first indication cell 1112 and the second indication cell 1114.

In some embodiments, the wearer or caregiver can remove a start tab 1122 of the potty training readiness indicator 1100. The removal of the start tab 1122 can expose the first expanding indicator 1140 to any moisture that the potty training readiness indicator 1100 will experience. In some embodiments, the caregiver or wearer may not need to remove a start tab. Upon a first wetness event, the expanding indicator 1140 can expand thereby breaking the separation wall 1150 between the first indication cell 1112 and the second indication cell 1114. Breaking the separation wall 1150 between the first indication cell 1112 and the second indication cell 1114 can allow liquid from a second wetness event to contact and activate the second expanding indicator 1142.

Similar to the first expanding indicator 1140, upon a second wetness event, the second expanding member 1144 can expand thereby breaking a separation wall 1152 between the second indicating cell 1114 and the third indicating cell 1116. Breaking the separation wall 1152 between the second indicating cell 1114 and the third indicating cell 1116 can allow liquid from a third wetness event to contact and activate the third expanding indicator 1144. Separation walls 1154, 1156, etc. are also considered in the present invention.

Any suitable material listed above for the expanding members or expanding indicators can be utilized in these embodiments. For example, the expanding members and/or expanding indicators may comprise AGM.

The reactive elements and reactive layers described heretofore may comprise a plurality of components such as a plurality of particles or printed pattern components. As an example, a reactive element, along with all of the reactive elements and reactive layers of the present invention, may include an indicating component and a urine sensitive component that function together to provide the caregiver a visual indication of the number of wetness events. The urine sensitive component may be utilized such that moisture which is not from a wetness event, i.e. urination, does not trigger the indication. For example, the urine sensitive component may be utilized such that perspiration from the wearer does not trigger a visible indication of a wetness event. Note that the urine sensitive component can be used in conjunction with the materials discussed with regard to the non-reactive elements, non-reactive portions, barrier layers, and protective layers.

In one embodiment, the indicating component may be in the form of particles suspended in the urine sensitive component. Moisture from a wetness event can activate the urine sensitive component, thereby causing the indicating component to provide a visible indication of the wetness event. The indicating component and the urine sensitive component can be separate and different components from each other.

A reactive element 910, or reactive layer, may be disposed on or in a substrate, or carrier elements. The carrier elements may comprise a web-like component such as a film, woven, or nonwoven material, foam, scrim, or cellulosic material, to which a urinary sensitive component or element is applied or affixed. Alternately, the carrier elements may enclose or encapsulate the urine sensitive component to prevent its migration or loss within the article before or during use. The carrier elements may each comprise one layer folded back upon itself or may each comprise a multiplicity of layers. If more than one layer is employed, the various layers may have different properties or comprise different materials. For example, the urine sensitive component may be disposed between a permeable top (i.e., wearer-facing) layer and an impermeable bottom layer. The indicating component may be in the form of particles suspended in the urine sensitive component. The top layer may alternatively comprise a selectively permeable layer, a dissolving layer, a pH sensitive layer, or a coating. The carrier elements may be flexible or may be relatively rigid.

The indicating component of the reactive elements 910 may comprise a colorant, dye, or indicator that changes appearance (e.g., color) upon contact with urine. Examples of suitable indicating components include food grade dyes such as FD&C No. 1 Blue and pH indicators such as bromocresol green, bromophenol blue, and resazorine. Any suitable indicating component may be utilized including those materials discussed heretofore with regard to the indicating elements and/or indicating members.

Further, any of the aforementioned methods may be used alone or in combination. For example, the potty training readiness indicator of the present invention may comprise a single indicating member or a plurality of indicating members. The single indicating member 870 can provide a first signal for a first wetness event and a second signal, which is different from the first signal, for a second wetness event. For example, a first wetness event may cause a first signal which is a visible indication that is yellow, while a second wetness event, may cause a second signal which is a separate visible indication which is blue or green. Therefore the caregiver could see a yellow indication and a blue indication which correlates to the first and second wetness events, respectively. In yet another example, the second signal can modify the first signal, e.g. yellow combines with blue to form green, to provide a single visible indication of the second wetness event.

Embodiments are contemplated where a first indication is provided for a first wetness event and a subsequent indication is provided when the number of wetness events is greater than one. Also, embodiments, are contemplated where a first indication is provided for a first wetness event, a second indication is provided for a second wetness event, and a subsequent indication is provided when the number of wetness events exceeds two.

Additionally, embodiments where graphics or visible indications are initially present and become obstructed when wetted are contemplated. For example, the disposable absorbent article, when dry, may comprise a plurality of indicating members providing a plurality of visible indications which are blue. Upon a first wetness event, a first indicating member can dissipate such that the visible indication of the first indicating member is obstructed through the backsheet. Similarly, upon a second wetness event the visible indication of a second indicating member can dissipate such that the visible indication of the second indicating member is obstructed through the backsheet.

Any suitable material can be utilized to provide visible indication when dry and obstructed indication or no indication when wet. For example, the indicating members may comprise an ink which is visible when the disposable article is in a dry state and which dissipates when wetted. Some suitable examples include an ink available under the designation CRNFS 561179 which is available from Sun Chemical® and an ink available under the designation 5307 which is available from Videojet®.

Other embodiments including graphics or visible indications which are initially present and become obstructed when wetted are contemplated. For example, the disposable absorbent article, when dry, may comprise a plurality of indicating members which provide yellow visible indications. Upon a first wetness event, the visible indication of the first indicating member can turn blue. In some embodiments, a background may comprise a first color which matches the activated color of the indicating member, e.g. blue, such that the activated color is not distinguishable from the color of the background. For example, an indicating member can provide a yellow indication when dry and a blue indication when activated. So, as an example, a blue background can be chosen such that upon a wetness event, the blue indication would be indistinguishable from the blue background. In another embodiment, the indicator may comprise a swellable material and upon wetness, the material expands to cover a graphic on the indicator, such that the graphic is no longer visible.

Any suitable material can be utilized to provide visible indications when dry and a different visible indication when wet. For example, some materials, as discussed in the example above can provide an initially yellow indication when dry; however, upon being wetted can provide a blue visible indication. Some suitable examples of materials which can provide a first visible indication when dry and a second visible indication (different from the first visible indication) when wet are sold under the designation of H9219-01, H9052, and H9133-05, available from Bostik®.

In some embodiments, the first indicating member may comprise a combination of two dyes which form a first color. For example, the dyes can be selected such that a first dye or the second dye is water soluble. Therefore, upon a wetness event, the first dye or the second dye can dissolve. In doing so, the visible indication can change from a first color to a second color. As an example, the two dyes may comprise yellow and blue such that the first color of the visible indication is green. Upon a wetness event, the blue dye can be selected such that the blue dye dissolves and the yellow dye does not dissolve. Thus, the visible indication can change from green to yellow upon a wetness event. In another embodiment, a graphic may be covered with a film that dissolves upon a wetness event such that the graphic appears after the wetness event.

In another embodiment, the indicating member may comprise the urine sensitive component which is applied as a stripe or layer to a flexible substrate, such as a film. Plasticizers such as glycerol diacetate may be utilized to prevent the indicating member, or any component thereof, from cracking under mechanical stress and leading to false positives or negatives. In the context of a potty training readiness indicator, a plasticizer may comprise any compound or composition that is at least partially soluble or miscible in the urine sensitive component and that reduces the tendency of the component to form crystallized regions, thereby reducing the glass transition temperature of the component and increasing its flexibility in the temperature range in which the article is expected to be used. Additional non-limiting examples of suitable plasticizers include polyhydroxy compounds such as glycerol and polyethylene glycols, microcrystalline waxes, ethylene vinyl acetates, isoparaffins, Guerbet alcohols, branched esters, branched alcohols, and other compounds such as those described above.

The indicating members, or any of the components, elements, or layers thereof, may be applied to a substrate, such as the article or any component thereof, or to a carrier element, via any means known in the art. Suitable processes for applying indicating members, components thereof, or elements thereof in a liquid or molten state to a substrate in either a continuous mode, intermittent mode, or in patterns, include slot coating, gravure printing, inkjet printing, spraying, screening, and the like. The indicating members, components thereof, elements thereof, or layers thereof, may be applied to a substrate or article in a solid form, such as films, webs, fibers, or particles, via continuous unwind processes, cut & slip processes, air deposition, and the like, and may be joined to the substrate via physical entanglement, entrapment, adhesives, or any other means as known in the art.

The urine sensitive component preferably changes properties in the presence of urine or is at least partially permeable by urine. For example, the urine sensitive component may dissolve or become more permeable in the presence of urine. The urine sensitive component may sense, or respond to, any of the components or properties of urine, including water, ion content, organic chemical content, ionic strength, pH, enzymes, urea, etc. Suitable materials for use in the urine sensitive component include starches and sugars, polyvinyl alcohol (in situ formed films and pre-manufactured films), gelatins, and other water or pH soluble films or materials. Other suitable materials include wetness or urine indicating compositions as known in the art, such as hot melt wetness indicators, water soluble dye systems, etc., including those described in U.S. Pat. Nos. 4,022,211; 4,743,238; 5,066,711; 5,342,861; 4,681,576; 5,035,691; 4,231,370; 4,895,567; and 6,075,178. Additionally, novel urine indicating compositions, such as those described U.S. Pat. No. 6,772,708 for a Wetness Indicator Having Improved Colorant Retention, may be employed as the urine sensitive component. For example, the urine sensitive component may comprise stearyl alcohol, microcrystalline waxes, etholxylated alcohols, cationic quaternary amines, or mixtures thereof, and an indicating component, such as a pH indicator. In another example, the urine sensitive component may comprise a material or composite having different optical properties (e.g., contrast) in the wet state versus the dry state. For this example, the urine sensitive component may include films or tissues having patterns printed in permanent ink which appear, when viewed through the backsheet, darker when wetted thereby obviating the need for the indicating component.

Suitable material for use as the counter-acting elements are those materials listed as suitable for the non-reactive members, those materials listed as suitable for the indicating component, those materials listed as suitable for the urine sensitive component, or any combination thereof. Optionally, the counter-acting elements may comprise any material known in the art for modifying a visible signal of an indicating member.

A different signal or different visible indication as discussed herein can be a different color, shape, design, pattern, or combination thereof. Additionally, a different signal or a different visible indication may be longitudinally or laterally displaced from another signal and can be the same or a different color, shape, design, or pattern, as that signal. For example, a first signal may comprise a yellow dot. A second signal may similarly comprise a yellow dot; however, the second signal may be longitudinally or laterally displaced from the first signal.

Despite the fact that the embodiments and examples discussed heretofore disclose a signal of the potty training readiness indicator which provides a visible indication of the wetness events, signals of the present invention can include many different types of indications as mentioned previously. Similar embodiments and examples to those discussed above are available with regard to a signal which comprises an indication which is visible, audible, tactile, olfactory, or a combination thereof. For example, high surface area foams as further described in U.S. Pat. Nos. 5,387,207; 5,650,222; 6,013,589; and 6,083,211, can be used to provide a tactile indication of a wetness event. Any devices, chemistries, etc., known in the art to produce visible, olfactory, audible, or tactile indications can be used in the present invention.

Furthermore, the present invention is directed to a method of indicating potty training readiness. This method may include the steps of a) placing an absorbent article comprising a potty training readiness indicator about the lower torso of a wearer; b) checking the absorbent article during wear to determine if a wetness event has occurred; and c) determining if the wearer is ready for potty training based on a signal selected from the group consisting of the number of wetness events having occurred in a pre-determined period of time, the time until a first wetness event, and the spread of activation of said indicator across the area of said absorbent article. The method may further comprise the step of initiating the start time of the indicator by removing a protective strip on the indicator. The method may further comprise the step of initiating the start time of the indicator by squeezing the indicator.

A variety of materials can be utilized in the manufacture of the absorbent articles described herein. Some examples of the materials which can be used in the manufacture of absorbent articles are provided below; however, the list of materials provided is by no means exhaustive. For example, breathable materials, which are used extensively in absorbent articles may include materials such as woven webs, nonwoven webs, composite materials such as film-coated nonwoven webs, microporous films such as manufactured by Mitsui Toatsu Co., of Japan under the designation ESPOIR NO™ and by Exxon Chemical Co., of Bay City, Tex., U.S.A. under the designation EXXAIRE™, and monolithic films such as manufactured by Clopay Corporation, Mason, Ohio, U.S.A. under the name HYTREL™ blend P18-3097. Some breathable composite materials are described in greater detail in U.S. Pat. Nos. 6,187,696; 5,938,648; 5,865,823; and 5,571,096.

The backsheet is generally that portion of the diaper positioned adjacent a garment-facing surface of the absorbent core that prevents the exudates absorbed and contained therein from soiling articles that may contact the diaper, such as bedsheets and undergarments. The topsheet is preferably positioned adjacent body-facing surface of the absorbent core and may be joined thereto and/or to the backsheet by any attachment means known in the art. The topsheet, the backsheet, and the absorbent core may be assembled in a variety of configurations, as further described generally in U.S. Pat. Nos. 3,860,003, 5,151,092, 5,221,274, 5,554,145, 5,569,234, 5,580,411, and 6,004,306.

The absorbent core may comprise any absorbent material which is generally compressible, conformable, non-irritating to the wearer's skin, and capable of absorbing and retaining liquids such as urine and other certain body exudates. The absorbent core may be manufactured in a wide variety of sizes and shapes and may comprise a wide variety of liquid-absorbent materials commonly used in disposable diapers and other absorbent articles such as comminuted wood pulp, which is generally referred to as airfelt. Examples of other suitable absorbent materials include creped cellulose wadding; meltblown polymers, including coform; chemically stiffened, modified or cross-linked cellulosic fibers; tissue, including tissue wraps and tissue laminates; absorbent foams; absorbent sponges; superabsorbent polymers; absorbent gelling materials; or any other known absorbent material or combinations of materials. Exemplary absorbent structures for use as the absorbent core are described in U.S. Pat. Nos. 4,610,678, 4,673,402, 4,834,735, 4,888,231, 5,137,537, 5,147,345, 5,342,338, 5,260,345, 5,387,207, and 5,625,222.

One preferred embodiment of the present invention includes, but is not limited to, articles described in U.S. Patent Application No. 2004/0162536 and U.S. Patent Application No. 2004/0167486. The aforementioned applications are directed to absorbent articles having an absorbent core which imparts increased wearing comfort to the article and makes it thin and dry.

As noted above, the diaper may also include a fastening system. The fastening system preferably maintains the first waist region and the second waist region in a configuration so as to provide lateral tensions about the circumference of the diaper to hold the diaper on the wearer. The fastening system preferably comprises a surface fastener such as tape tabs, hook and loop fastening components and/or hermaphroditic fastening components, although any other known fastening means are generally acceptable. In alternative embodiments, opposing sides of the article may be seamed or welded to form a pant. This allows the article to be used as a pull-on type diaper, such as a training pant.

Some exemplary surface fastening systems are disclosed in U.S. Pat. Nos. 3,848,594, 4,662,875, 4,846,815, 4,894,060, 4,946,527, 5,151,092, and 5,221,274. An exemplary interlocking fastening system is disclosed in co-pending U.S. Pat. No. 6,432,098. The fastening system may also: provide a means for holding the article in a disposal configuration as disclosed in U.S. Pat. No. 4,963,140; include primary and secondary fastening systems, as disclosed in U.S. Pat. No. 4,699,622; provide means to reduce shifting of overlapped portions or to improve fit as disclosed in U.S. Pat. No. 5,242,436; and provide means to resist gapping at a wearer's belly as disclosed in U.S. Pat. Nos. 5,499,978, 5,507,736, and in 5,591,152.

Examples of diapers with elasticized side panels are disclosed in U.S. Pat. Nos. 4,857,067, 4,381,781, 4,938,753, 5,151,092, 5,221,274, 5,669,897, and 6,004,306.

Suitable absorbent and nonabsorbent sublayers are described in European Patent Application No. EP 0 847 738 A1 and U.S. Pat. No. 5,941,864. Further, the sublayer, or any portion thereof, may include or be coated with a lotion or other known substances to add, enhance or change the performance or other characteristics of the element.

Embodiments of the present invention may also include pockets for receiving and containing waste, spacers which provide voids for waste, barriers for limiting the movement of waste in the article, compartments or voids which accept and contain waste materials or any combinations thereof. Examples of pockets and spacers for use in absorbent products are described in U.S. Pat. Nos. 5,514,121, 5,171,236, 5,397,318, 5,540,671, 6,168,584, 5,306,266, and 5,997,520. Examples of compartments or voids are disclosed in U.S. Pat. Nos. 4,968,312, 4,990,147, 5,062,840, and 5,269,755. Examples of suitable transverse barriers are described in U.S. Pat. Nos. 5,554,142, 6,010,490, and 5,653,703. Examples of other structures especially suitable for management of low viscosity feces are disclosed in U.S. Pat. Nos. 5,941,864, 5,977,430, and 6,013,063.

EXAMPLES

An indicating member suitable for use in a disposable absorbent article may be constructed as follows. Other indicating members suitable for use in a disposable absorbent article are described in U.S. patent application Ser. Nos. 11/100,653 and 11/400,633.

1. An indicating composition can be prepared according to the formula and procedure described below:

| Ingredient | Grams |
| --- | --- |
| Stearyl Alcohol | 49.8 |
| Microcrystalline Wax | 10.0 |
| Stearyl Phosphate | 10.0 |
| Dimethyl(2-ethylhexylhydrogenated tallowalkyl)ammonium methyl sulfate | 10.0 |
| Bromocresol Green (powdered acid form) | 0.2 |
| C20-C40 Pareth-40 nonionic surfactant | 20.0 |

This urine indicating composition is made by first weighing out the correct amounts of stearyl alcohol, microcrystalline wax, and stearyl phosphate into a stainless steel container. The stearyl alcohol should be a white waxy solid with a purity of at least 97% and no more than 2% of arachidyl alcohol, and have a melting point in the range of about 56° C. to about 60° C. The product designated C01897 stearyl alcohol available from The Procter & Gamble Company of Cincinnati, Ohio, U.S.A., is a current example of a suitable material. The microcrystalline wax should be a high molecular weight petroleum based wax consisting of saturated branched and cyclic non-polar hydrocarbons and possessing a melting point in the range of about 60° C. to about 95° C. The product designated MULTIWAX™ W-835 available from the Crompton Corporation of Petrolia, Pa., U.S.A. is an example of a suitable microcrystalline wax. This mixture is heated and mixed at a temperature in the range of about 100° C. to about 110° C. until the mixture is a clear, transparent and colorless molten mixture. The dimethyl(2-ethylhexylhydrogenated tallowalkyl)ammonium methyl sulfate is then added to the above molten mixture and heated at a temperature in the range of about 100° C. to about 110° C. for 10 minutes. The dimethyl(2-ethylhexylhydrogenated tallowalkyl)ammonium methyl sulfate should have a quaternary salt content of 81.5-84.5%, possess a free amine and free amine salt impurity content of no more than 4%, and have an HLB of 17-18. The product designated ARQUAD™ HTL8(W)-MS available from Akzo-Nobel of Chicago, Ill., U.S.A. is a good example of a dialkyldimethyl quaternary ammonium salt currently meeting these requirements. To this mixture, the bromocresol green pH indicator is added. The resultant mixture is heated while mixing at a temperature in the range of about 100° C. to about 110° C. for 20 mixtures. Finally, to this mixture, C20-C40 Pareth-40 surfactant is added, the surfactant having been preheated to a temperature in the range of about 100° C. to about 110° C. The C20-C40 Pareth-40 surfactant should have molecular weight ($M_n$) between about 2200 and about 2400, an ethylene oxide content between in the range of about 75% to about 85%, an HLB of approximately 16, and a melting point in the range of about 80° C. to about 94° C. The product designated PERFORMATHOX™ 480 available from New Phase Technologies of Sugar Land, Tex., U.S.A is an example of a suitable C20-C40 Pareth-40 meeting these requirements. The entire composition is subsequently heated at a temperature in the range of about 100° C. to about 110° C. until it is clear, transparent and yellow-orange in color.

2. A 5 mm wide stripe of the composition from step 1 above is applied to the inner surface of a 1.0 mil thick polypropylene film is coated with at a basis weight of 26 grams per square meter and width of 5 millimeters.

3. After the film from step 2 has solidified, it is completely covered by a continuous layer of 1-tetradecanol. This 1-tetradecanol layer has a basis weight of between 26 to 39 grams per square meter, and a width of 15 millimeters. The 1-tetradecanol layer is oriented such that its width extends 5 mm on either side of the width of the indicating composition layer.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article adapted for wearing about the lower torso of a wearer, the absorbent article comprising a chassis, said chassis comprising;
  a. a topsheet;
  b. a backsheet attached to at least a portion of said topsheet;
  c. an absorbent core disposed between said topsheet and said backsheet; and d. a potty training readiness indicator attached to said chassis, wherein said indicator is adapted to provide a visible indication of when the wearer is ready to be potty trained;

wherein said indicator measures the amount of time from a start time until a first wetness event;

wherein said indicator comprises a moving time line having a colored bar;

wherein said indicator is adapted to allow a caregiver to initiate said start time, causing the colored bar to begin moving across the moving time line; and wherein upon a wetness event occurring in the absorbent article, the colored bar stops moving across the moving time line.

2. The absorbent article of claim 1, wherein said indicator counts and displays the number of wetness events.

3. The absorbent article of claim 1, wherein said indicator comprises a plurality of indicating members, wherein a first wetness event is capable of activating one or more of said indicating members.

4. The absorbent article of claim 3, wherein a second wetness event is capable of activating one or more of said indicating members.

5. The absorbent article of claim 1, wherein said indicator comprises a plurality of indicating members, wherein a first wetness event is capable of activating a first indicating member thereby causing said first indicating member to provide a first signal in a first area of said article.

6. The absorbent article of claim 5, wherein a second wetness event is capable of activating a second indicating member thereby causing said second indicating member to provide a second signal in a second area of said article.

7. The absorbent article of claim 5, wherein said first signal is selected from the group consisting of a change of color of said first indicating member, disappearing color of said first indicating member, appearing color of said first indicating member, and tactile change of said first indicating member.

8. The absorbent article of claim 6, wherein said second signal is selected from the group consisting of a change of color of said second indicating member, disappearing color of said second indicating member, appearing color of said second indicating member, and tactile change of said second indicating member.

9. The absorbent article of claim 6, wherein said first signal and said second signal are the same.

10. The absorbent article of claim 6, wherein said first signal and said second signal are different.

11. The absorbent article of claim 1, wherein the movement of the time line is stopped through a mechanism that gels upon contact with urine or a component thereof.

12. The absorbent article of claim 1, the movement of the time line is stopped through the use of a substrate that swells upon contact with urine, thus preventing liquid comprised within the moving time line from any further flow.

13. The absorbent article of claim 1, wherein said indicator is adapted to allow a caregiver to initiate said start time by removing a protective strip from said indicator.

14. The absorbent article of claim 1, wherein said indicator is adapted to allow a caregiver to initiate said start time by squeezing the indicator.

* * * * *